(12) United States Patent
Legrand et al.

(10) Patent No.: US 8,241,370 B2
(45) Date of Patent: Aug. 14, 2012

(54) COMPOSITION COMPRISING AN ALKANOLAMINE, A BASIC AMINO ACID AND A SUITABLY SELECTED ADDITIONAL ALKALINE AGENT

(75) Inventors: Frédéric Legrand, Westfield, NJ (US); Jean-Marc Ascione, Paris (FR)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 12/809,062

(22) PCT Filed: Dec. 17, 2008

(86) PCT No.: PCT/EP2008/067785
§ 371 (c)(1),
(2), (4) Date: Feb. 25, 2011

(87) PCT Pub. No.: WO2009/080667
PCT Pub. Date: Jul. 2, 2009

(65) Prior Publication Data
US 2011/0150797 A1   Jun. 23, 2011

Related U.S. Application Data

(60) Provisional application No. 61/006,535, filed on Jan. 18, 2008.

(30) Foreign Application Priority Data

Dec. 20, 2007   (FR) ...................................... 07 60127

(51) Int. Cl.
*A61Q 5/10* (2006.01)

(52) U.S. Cl. ............. 8/405; 8/406; 8/431; 8/435; 8/455; 8/597; 8/604; 8/619; 8/620

(58) Field of Classification Search .............. 8/405, 406, 8/431, 435, 455, 597, 604, 619, 620
See application file for complete search history.

(56) References Cited

U.S. PATENT DOCUMENTS
2005/0188480 A1* 9/2005 Lim et al. .......................... 8/405

FOREIGN PATENT DOCUMENTS
| DE | 10 2005 059 647 A1 | 6/2007 |
| JP | 2004-262886 | 9/2004 |
| WO | WO 97/04739 | 2/1997 |

OTHER PUBLICATIONS

French Search Report for FR 0760127, dated Aug. 13, 2008.
English language abstract of DE 10 2005 059 647 A1, Jun. 14, 2007.
English language abstract of JP 2004-262886, Sep. 24, 2004.
English language abstract of WO 97/04739, Feb. 13, 1997.

* cited by examiner

*Primary Examiner* — Eisa Elhilo
(74) *Attorney, Agent, or Firm* — O'Brien Jones PLLC

(57) ABSTRACT

The present invention relates to a composition for treating keratin fibers, and in particular human keratin fibers such as the hair, comprising, in a cosmetically acceptable medium, one or more alkanolamines, one or more basic amino acids and one or more additional alkaline agents chosen from aqueous ammonia; ammonium salts of acids whose pKa at 25° C. is greater than 4; alkali metal or alkaline-earth metal hydroxides, carbonates, carbamates and hydrogen carbonates. The present invention also relates to processes for bleaching and/or dyeing keratin fibers, and also to multi-compartment devices or 'kits' for performing these processes.

15 Claims, No Drawings

COMPOSITION COMPRISING AN ALKANOLAMINE, A BASIC AMINO ACID AND A SUITABLY SELECTED ADDITIONAL ALKALINE AGENT

CROSS REFERENCE TO RELATED APPLICATIONS

This application is a National Phase application based on PCT/EP2008/067785 filed on Dec. 17, 2008, and claims the priority of French Application No. 0760127, filed on Dec. 20, 2007, and the benefit of U.S. Provisional Application No. 61/006,535, filed on Jan. 18, 2008, the content of all of which is incorporated herein by reference.

The present invention relates to a composition for treating keratin fibres, and in particular human keratin fibres such as the hair, comprising, in a cosmetically acceptable medium, one or more alkanolamines, one or more basic amino acids and one or more additional alkaline agents chosen from aqueous ammonia; ammonium salts of acids whose pKa at 25° C. is greater than 4; alkali metal or alkaline-earth metal hydroxides, carbonates, carbamates and hydrogen carbonates.

It is known practice to use oxidizing compositions for treating the hair, especially for dyeing human keratin fibres, and in particular the hair, with dye compositions containing oxidation dye precursors, which are generally known as oxidation bases. These oxidation bases are colourless or weakly coloured compounds, which, when combined with oxidizing products, give rise to coloured compounds via a process of oxidative condensation.

The oxidation dyeing process consists in applying to keratin fibres oxidation bases or a mixture of oxidation bases and couplers with an oxidizing agent, such as hydrogen peroxide (or aqueous hydrogen peroxide solution), which is added at the time of use.

Generally, this process is performed at an alkaline pH, especially in the presence of aqueous ammonia, and can produce dyeing and simultaneous lightening of the fibre, which is reflected in practice by the possibility of obtaining a final coloration that is lighter than the original colour. In addition, lightening of the fibre has the advantageous effect of generating a unified colour in the case of depigmented hair, and, in the case of naturally pigmented hair, of bringing out the colour, i.e. making it more visible.

It is also known practice to dye human keratin fibres via "semi-permanent" dyeing or direct dyeing, which involves dyes that are themselves capable of effecting a more or less pronounced modification of the natural coloration of the hair.

These direct dyes may also be used in combination with oxidizing agents, when it is desired to obtain a coloration that is lighter than the original colour of the fibres. Thus, these direct dyes may be used in lightening direct dye compositions based on aqueous hydrogen peroxide solution and aqueous ammonia or in oxidation dyeing compositions in combination with oxidation bases and/or couplers.

Moreover, when a person wishes to bleach his hair, it is also known practice to perform the bleaching using lightening products based on aqueous ammonia and hydrogen peroxide.

Thus, it is common practice to make use of alkaline oxidizing compositions based on hydrogen peroxide and aqueous ammonia for dyeing and/or bleaching human keratin fibres, and in particular the hair.

However, although these working conditions prove to be efficient, they may lead to a certain amount of unpleasantness at the time of use.

In particular, when these compositions are applied to the hair, there is generally a release of ammonia, which may lead to a suffocating odour and irritation to the eyes, the respiratory pathways and mucous membranes.

Furthermore, ammonia may cause, especially in the case of people with a sensitive scalp, discomfort reactions such as redness, itching or stinging.

Finally, ammonia, in combination with the oxidizing agent, may also contribute towards damaging the keratin fibres. Specifically, over time, it is observed that the fibres are more or less degraded and have a tendency to become coarse, dull, brittle and difficult to style.

Thus, to overcome all the drawbacks described above, numerous alternatives have already been proposed in order to significantly reduce the content of ammonia in compositions intended for dyeing and/or bleaching fibres.

To this end, it has been proposed to apply to the hair dyeing and/or bleaching compositions comprising a non-volatile organic amine, such as monoethanolamine. Although such compositions have the advantage of not giving off ammonia during their use, they usually cause discomfort reactions, in particular irritation in the case of people with a sensitive scalp. Furthermore, for equivalent lightening performance qualities, monoethanolamine damages the hair more than aqueous ammonia.

Other compositions combining aqueous ammonia with a water-soluble ammonium salt have also been envisaged. Such compositions are especially described in patent application EP 0 148 466.

However, these compositions cannot satisfactorily reduce the unpleasant odours caused by the release of ammonia, and the lightening performance qualities of compositions of this type remain limited when compared with ammonia-based compositions.

Similarly, compositions containing compounds such as ammonium, alkali metal or alkaline-earth metal carbonates or hydrogen carbonates have been proposed.

Although these compositions allow the ammonia content to be significantly reduced, their lightening performance qualities still remain inferior to those of ammonia-based compositions. Furthermore, these compositions continue to strongly damage keratin fibres.

Alternatively, compositions based on neutral or basic amino acids have been envisaged in order to totally or partially replace the content of aqueous ammonia.

Thus, patent EP 0 840 593 describes ammonia-free compositions especially comprising, as alkaline agent, a mixture based on a compound chosen from amino acids and oligopeptides containing an amine group and a —COOH or —SO$_3$H group and a compound chosen from the group formed by monoethanolamine, monoisopropanolamine, 2-amino-2-methylpropanol, 2-amino-2-methyl-1,3-propanediol, 2-amino-2-ethyl-1,3-propanediol and 2-amino-2-methylbutanol.

Similarly, patent applications JP 2004-262 885 and JP 2004-262 886 describe ammonia-free compositions based on neutral or basic amino acids, non-volatile amine and an organic acid ammonium ion.

Finally, patent U.S. Pat. No. 5,131,912 describes compositions based on neutral or basic amino acids and alkaline agents such as ammonium or alkali metal or alkaline-earth metal hydrogen carbonates. The mixture before use of these alkaline compositions, with an oxidizing hydrogen peroxide composition, has a pH of between 6.5 and 7.9.

Although such compositions have the advantage of not giving off ammonia during their use, they still cannot equal the level of performance, in terms of lightening, of ammonia-based compositions. Furthermore, these compositions may cause irritation of the scalp.

Thus, there is a real need to reduce the content of aqueous ammonia in compositions intended especially for dyeing and/or bleaching, in order to reduce the unpleasant odours accompanying it, the irritation of the scalp and the damage to the keratin fibres, while at the same time maintaining good dyeing and/or bleaching properties.

One subject of the present invention is a composition for treating keratin fibres, comprising, in a cosmetically acceptable medium:
one or more alkanolamines;
one or more basic amino acids; and
one or more additional alkaline agents chosen from aqueous ammonia; ammonium salts of acids whose pKa at 25° C. is greater than 4; alkali metal or alkaline-earth metal hydroxides, carbonates, carbamates and hydrogen carbonates;
the alkanolamines/basic amino acids mole ratio being less than or equal to 10.

The composition according to the invention has the advantage of minimizing or even eliminating the drawbacks caused by the release of ammonia.

The composition according to the invention can also reduce the discomfort that may be experienced at the time of application of the said composition to the keratin fibres on the scalp.

Furthermore, the composition allows a reduction in damage to the fibre in comparison with conventional dyeing/bleaching compositions containing ammonia as principal alkaline agent.

When it is used with oxidation bases and/or couplers and/or direct dyes, a dye composition is obtained that has the additional advantage of having good dyeing properties, especially powerful, chromatic, sparingly selective colorations that show good resistance to the various attacking factors to which hair may be subjected.

When the composition according to the invention is used with an oxidizing agent, such as hydrogen peroxide, a bleaching or lightening composition is obtained that has the additional advantage of giving satisfactory lightening of keratin fibres.

A subject of the present invention is also processes for bleaching and/or dyeing keratin fibres, and also multi-compartment devices or "kits" for performing these processes.

Other subjects, characteristics, aspects and advantages of the invention will emerge even more clearly on reading the description and the examples that follow.

In the text hereinbelow, unless otherwise indicated, the limits of the indicated ranges are included in the invention.

According to one particular embodiment of the invention, the alkanolamine(s) is (are) chosen from monoethanolamine, triethanolamine, monoisopropanolamine, diisopropanolamine, N-dimethylaminoethanolamine, 2-amino-2-methyl-1-propanol, triisopropanolamine, 2-amino-2-methyl-1,3-propanediol, 3-amino-1,2-propanediol, 3-dimethylamino-1,2-propanediol and tris(hydroxymethyl) aminomethane.

Monoethanolamine is preferably used.

The alkanolamine(s) is (are) generally present in the composition in accordance with the invention in an amount of between 0.1% and 15% by weight, preferably between 0.5% and 10% by weight and more preferentially between 1% and 7% by weight relative to the total weight of the composition.

For the purposes of the present invention, the term "basic amino acid" means an amino acid comprising at least two amine functions, one of which may be included in a ring or may belong to a ureido group, and at least one acid function. The acid function(s) may be carboxylic, sulfonic, phosphonic or phosphoric, preferably carboxylic.

The basic amino acids present in the composition in accordance with the invention preferably have a molecular weight of less than 500.

According to one particular embodiment of the invention, the basic amino acids(s) is (are) chosen from basic amino acids whose lowest pKb value at 25° C. is less than 5.5.

The basic amino acid(s) is (are) chosen, for example, from those corresponding to formula (I) below:

$$R-CH_2-CH\begin{matrix}NH_2\\CO_2H\end{matrix} \qquad (I)$$

in which R denotes a group chosen from:

$$\begin{matrix}\text{imidazolyl};&-(CH_2)_3NH_2;&-(CH_2)NH_2;\\-(CH_2)NHCONH_2;&-(CH_2)_2NH-C(=NH)-NH_2\end{matrix}$$

The compounds corresponding to formula (I) are histidine, lysine, arginine, ornithine and citrulline.

Preferably, the basic amino acids(s) is (are) chosen from histidine, arginine and lysine.

The composition in accordance with the invention generally has a basic amino acid(s) concentration of between 0.1% and 15% by weight, preferably between 0.5% and 10% by weight and more preferentially between 1% and 10% by weight relative to the total weight of the composition.

According to one particular embodiment of the invention, the alkanolamines/basic amino acids mole ratio is greater than or equal to 0.1 and preferably greater than or equal to 1. Even more preferentially, this ratio is greater than or equal to 1.5.

According to one particular embodiment of the invention, the ammonium salt(s) that may be present in the composition is (are) ammonium salts of a mineral acid or of an organic acid containing from 1 to 7 carbon atoms, the said acid having a pKa at 25° C. of greater than 4.

Examples of such ammonium salts that may especially be mentioned include ammonium carbonate, ammonium carbamate, ammonium hydrogen carbonate and ammonium acetate.

Preferably, the ammonium salt(s) is (are) chosen from ammonium carbonate, ammonium acetate and ammonium hydrogen carbonate. Even more preferentially, the ammonium salt(s) is (are) chosen from ammonium carbonate and ammonium acetate.

The alkali metals or alkaline-earth metals may be chosen from lithium, sodium, potassium, magnesium, calcium and barium.

Alkali metal or alkaline-earth metal hydroxides that may especially be mentioned include lithium, sodium, potassium, magnesium, calcium, strontium and/or barium hydroxides.

Preferably, the alkali metal or alkaline-earth metal hydroxides are chosen from potassium hydroxide, sodium hydroxide and magnesium hydroxide.

Preferably, the alkali metal or alkaline-earth metal carbonates and hydrogen carbonates are chosen from sodium carbonate, magnesium carbonate, potassium carbonate, sodium bicarbonate and potassium bicarbonate.

Preferably, the alkali metal or alkaline-earth metal carbamates are chosen from sodium carbamate and potassium carbamate.

According to one particular embodiment of the invention, the additional alkaline agent(s) is (are) chosen from aqueous ammonia, ammonium acetate, ammonium carbonate, sodium carbonate, potassium carbonate, sodium hydroxide and potassium hydroxide.

The additional alkaline agent(s) may be present in the composition according to the invention in a concentration ranging from 0.1% to 15% by weight and preferably from 0.5% to 10% relative to the total weight of the composition.

According to one particular embodiment of the invention, the composition comprises monoethanolamine, one or more basic amino acids and aqueous ammonia.

Preferably, the composition in accordance with the invention comprises monoethanolamine, arginine and aqueous ammonia.

According to another particular embodiment of the invention, the composition comprises monoethanolamine, one or more basic amino acids and one or more ammonium salts of acids whose pKa at 25° C. is greater than 4. Preferably, the ammonium salt(s) is (are) chosen from ammonium carbonate and ammonium acetate. Even more preferentially, the composition in accordance with the invention comprises one of the following combinations:

monoethanolamine, lysine and ammonium carbonate;
monoethanolamine, lysine and ammonium acetate; or
monoethanolamine, histidine and ammonium acetate.

According to another particular embodiment, the composition comprises 2-amino-2-methyl-1-propanol, one or more basic amino acids and aqueous ammonia. Preferably, the composition in accordance with the invention comprises 2-amino-2-methyl-1-propanol, arginine and aqueous ammonia.

According to another particular embodiment, the composition in accordance with the invention comprises monoethanolamine, one or more amino acids and one or more additional alkaline agents chosen from alkali metal and alkaline-earth metal hydroxides and carbonates. Preferably, the composition in accordance with the invention comprises one of the following combinations:

monoethanolamine, arginine and potassium hydroxide; or
monoethanolamine, lysine and potassium carbonate.

The composition in accordance with the invention may comprise one or more oxidizing agents chosen, for example, from hydrogen peroxide, urea peroxide, alkali metal bromates, persalts such as perborates and persulfates, and enzymes such as peroxidases and two-electron or four-electron oxidoreductases. The use of hydrogen peroxide is particularly preferred.

The content of oxidizing agents in the composition may be between 0.1% and 10% by weight of the composition and preferably between 0.5% and 6% by weight of the composition.

The pH of the composition after mixing with the oxidizing agent is generally between 5.5 and 10.5 and preferably between 6 and 10.

The composition in accordance with the invention may comprise one or more surfactants chosen from anionic, nonionic, cationic, amphoteric and zwitterionic surfactants.

The composition according to the invention may also contain one or more fatty substances. The fatty substance(s) that may be used in the context of the present invention is (are) especially chosen from plant oils, animal oils, mineral oils, natural or synthetic oils, and fatty alcohols, and mixtures thereof.

The composition according to the invention may also contain one or more thickeners, also known as "rheology modifiers".

Non-associative gelling agents may be used as rheology modifiers; among these agents are colloidal silicates, polyethylene glycols, polyvinylpyrrolidones and hydrophilic silica gels.

The rheology modifiers may also be chosen from fatty acid amides (coconut monoethanolamide or diethanolamide, or oxyethylenated alkyl ether carboxylic acid monoethanolamide), cellulose-based thickeners (hydroxyethylcellulose, hydroxypropylcellulose or carboxymethylcellulose), guar gum and derivatives thereof (hydroxypropyl guar), gums of microbial origin (xanthan gum or scleroglucan gum), crosslinked acrylic acid or acrylamidopropanesulfonic acid homopolymers or copolymers, and associative thickening polymers.

These associative polymers are water-soluble polymers capable, in an aqueous medium, of reversibly combining with each other or with other molecules.

Their chemical structure comprises hydrophilic zones and hydrophobic zones characterized by at least one fatty chain.

Associative polymers may be of anionic, cationic, amphoteric or nonionic type.

Their concentration may range from about 0.01% to 10% and preferably from 0.1% to 5% by weight relative to the total weight of the composition according to the invention.

The composition according to the invention may also contain one or more anhydrous cationic or amphoteric conditioning polymers, for instance those described in French patents 2 788 974 and 2 788 976 and as described hereinbelow.

For the purposes of the present invention, the term "cationic polymer" denotes any polymer containing cationic groups and/or groups that can be ionized into cationic groups.

For the purposes of the present invention, the term "conditioning polymer" means a polymer that can improve the cosmetic properties of keratin fibres, such as the disentangling, the feel, the smoothness, the sheen and the volume.

The cationic polymers that may be used in accordance with the present invention may be chosen from any of those already known per se as improving the cosmetic properties of hair, namely, especially, those described in patent application EP-A-337 354 and in French patents FR-2 270 846, 2 383 660, 2 598 611, 2 470 596 and 2 519 863.

When they are present in the composition according to the present invention, the cationic and/or amphoteric polymers are present in a total weight proportion of less than or equal to 20%, preferably less than or equal to 8% and better still between 0.1% and 5% relative to the total weight of the composition.

For the purposes of the present invention, the term "cosmetically acceptable medium" means a medium that is compatible with keratin fibres and in particular the hair.

The medium that is suitable for the composition according to the invention is a cosmetically acceptable medium generally comprising water or a mixture of water and of one or more organic solvents. Examples of organic solvents that may be mentioned include $C_1$-$C_4$ lower alkanols, such as ethanol and isopropanol; polyols and polyol ethers, for instance 2-butoxyethanol, propylene glycol, glycerol, propylene glycol monomethyl ether, diethylene glycol monomethyl ether and monoethyl ether, and also aromatic alcohols, for instance benzyl alcohol or phenoxyethanol, and mixtures thereof.

The solvents are preferably present in proportions of between 1% and 40% by weight approximately, and even more preferentially between 5% and 30% by weight approximately, relative to the total weight of the cosmetic composition.

Needless to say, a person skilled in the art will take care to select this or these optional additional compound(s) such that the advantageous properties intrinsically associated with the composition in accordance with the invention are not, or are not substantially, adversely affected by the envisaged addition(s).

The composition according to the invention may be in various forms, such as in the form of liquids, creams or gels, or in any other form that is suitable for dyeing and/or bleaching keratin fibres, and especially human keratin fibres such as the hair.

The composition according to the invention may also comprise one or more oxidation bases and/or one or more couplers and/or one or more direct dyes.

When the composition according to the invention comprises one or more oxidation bases and/or one or more couplers and/or one or more direct dyes, the said composition is then a dye composition.

When the dye composition comprises, as dye(s), one or more oxidation bases optionally combined with one or more couplers, the said composition is then an oxidation dye composition.

By way of example, the oxidation bases are chosen from para-phenylenediamines, bis(phenyl)alkylenediamines, para-aminophenols, ortho-aminophenols and heterocyclic bases, and the addition salts thereof with an acid or with an alkaline agent.

Among the para-phenylenediamines that may be mentioned more particularly, for example, are para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl) amino-2-methylaniline, 4-N,N-bis(β-hydroxyethyl)-amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-paraphenylenediamine, 2-β-hydroxyethyloxy-para-phenylenediamine, 2-β-acetylaminoethyloxy-para-phenylenediamine, N-(β-methoxyethyl)-para-phenylenediamine and 4'-aminophenyl-1-(3-hydroxy) pyrrolidine, and the addition salts thereof with an acid or with an alkaline agent.

Among the para-phenylenediamines mentioned above, the ones most particularly preferred are para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine and 2-β-acetylamino-ethyloxy-para-phenylenediamine, and the addition salts thereof with an acid or with an alkaline agent.

Among the bis(phenyl)alkylenediamines that may be mentioned more particularly, for example, are N,N'-bis(β-hydroxyethyl)-N,N'-bis(4'-aminophenyl)-1,3-diaminopropanol, N,N'-bis(β-hydroxyethyl)-N,N'-bis(4'-aminophenyl) ethylenediamine, N,N'-bis(4-aminophenyl)-tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine and 1,8-bis(2,5-diaminophenoxy)-3,5-dioxa-octane, and the addition salts thereof with an acid or with an alkaline agent.

Among the para-aminophenols that may be mentioned more particularly, for example, are para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxy-methylphenol, 4-amino-2-aminomethylphenol, 4-amino-2-(β-hydroxyethylaminomethyl)phenol and 4-amino-2-fluorophenol, and the addition salts thereof with an acid or with an alkaline agent.

Among the ortho-aminophenols that may be mentioned more particularly, for example, are 2-aminophenol, 2-amino-5-methylphenol, 2-amino-6-methylphenol and 5-acetamido-2-aminophenol, and the addition salts thereof with an acid or with an alkaline agent.

Among the heterocyclic bases that may be mentioned more particularly, for example, are pyridine derivatives, pyrimidine derivatives and pyrazole derivatives, and the addition salts thereof with an acid or with an alkaline agent. Mention will be made most particularly of 1-β-hydroxyethyl-4,5-diaminopyrazole and 2,3-diamino-6,7-dihydro-1H,5H-pyrazolo[1,2-a] pyrazol-1-one, and the salts thereof.

When they are used, the oxidation base(s) preferably represent(s) from 0.005% to 15% by weight, and even more preferably from 0.01% to 10% by weight relative to the total weight of the composition.

If the dye composition according to the invention contains one or more oxidation bases, the said composition preferably contains one or more couplers conventionally used for dyeing keratin fibres. Among these couplers, mention may be made especially of meta-phenylenediamines, meta-aminophenols, meta-diphenols, naphthalene-based couplers and heterocyclic couplers, and the addition salts thereof with an acid or with an alkaline agent.

These couplers are more particularly chosen from 2-methyl-5-aminophenol, 5-N-(β-hydroxyethyl)amino-2-methylphenol, 3-aminophenol, 1,3-dihydroxybenzene, 1,3-dihydroxy-2-methylbenzene, 4-chloro-1,3-dihydroxy-benzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, sesamol, α-naphthol, 6-hydroxyindole, 4-hydroxyindole, 4-hydroxy-N-methylindole, 6-hydroxyindoline, 2,6-dihydroxy-4-methylpyridine, 1-H-3-methylpyrazol-5-one, 1-phenyl-3-methylpyrazol-5-one, 2,6-dimethylpyrazolo-[1,5-b]-1,2,4-triazole, 2,6-dimethyl[3,2-c]-1,2,4-triazole and 6-methylpyrazolo[1,5-a]benzimidazole, and the addition salts thereof with an acid or with an alkaline agent.

When they are present, the coupler(s) preferably represent(s) from 0.001% to 15% by weight and even more preferentially from 0.05% to 10% by weight relative to the total weight of the composition.

In general, the addition salts of the oxidation bases and couplers that may be used in the context of the invention are especially chosen from the addition salts with an acid, such as the hydrochlorides, hydrobromides, sulfates, citrates, succinates, tartrates, tosylates, benzenesulfonates, phosphates and acetates, and the addition salts with a base, such as sodium hydroxide, potassium hydroxide, ammonia, amines or alkanolamines.

When the dye composition does not comprise any oxidation bases or couplers, but only direct dyes, the composition is then an optionally lightening direct dye composition.

The direct dye(s) that may be used in the dye composition may be chosen from neutral, acidic or cationic nitrobenzene dyes, neutral, acidic or cationic azo direct dyes, neutral, acidic or cationic quinone and in particular anthraquinone direct dyes, azine direct dyes, triarylmethane direct dyes, indoamine direct dyes and natural direct dyes, alone or as a mixture.

Among the nitrobenzene direct dyes that may be used according to the invention, mention may be made, in a non-limiting manner, of the following compounds:
1,4-diamino-2-nitrobenzene
1-amino-2-nitro-4-β-hydroxyethylaminobenzene
1-amino-2-nitro-4-bis(βhydroxyethyl)aminobenzene
1,4-bis(β-hydroxyethylamino)-2-nitrobenzene
1-β-hydroxyethylamino-2-nitro-4-bis(β-hydroxyethylamino) benzene
1-β-hydroxyethylamino-2-nitro-4-aminobenzene
1-β-hydroxyethylamino-2-nitro-4-(ethyl)(β-hydroxyethyl)aminobenzene
1-amino-3-methyl-4-β-hydroxyethylamino-6-nitrobenzene
1-amino-2-nitro-4-β-hydroxyethylamino-5-chlorobenzene
1,2-diamino-4-nitrobenzene
1-amino-2-β-hydroxyethylamino-5-nitrobenzene
1,2-bis(β-hydroxyethylamino)-4-nitrobenzene
1-amino-2-tris(hydroxymethyl)methylamino-5-nitrobenzene
1-hydroxy-2-amino-5-nitrobenzene
1-hydroxy-2-amino-4-nitrobenzene
1-hydroxy-3-nitro-4-aminobenzene
1-β-hydroxyethyloxy-2-β-hydroxyethylamino-5-nitrobenzene
1-methoxy-2-β-hydroxyethylamino-5-nitrobenzene
1-β-hydroxyethyloxy-3-methylamino-4-nitrobenzene
1-β-γ-dihydroxypropyloxy-3-methylamino-4-nitrobenzene
1-β-hydroxyethylamino-4-β,γ-dihydroxypropyloxy-2-nitrobenzene
1-β,γ-dihydroxypropylamino-4-trifluoromethyl-2-nitrobenzene
1-β-hydroxyethylamino-4-trifluoromethyl-2-nitrobenzene
1-β-hydroxyethylamino-3-methyl-2-nitrobenzene
1-β-aminoethylamino-5-methoxy-2-nitrobenzene
1-hydroxy-2-chloro-6-ethylamino-4-nitrobenzene
1-hydroxy-2-chloro-6-amino-4-nitrobenzene
1-hydroxy-6-bis(β-hydroxyethyl)amino-3-nitrobenzene
1-βhydroxyethylamino-2-nitrobenzene
1-hydroxy-4-β-hydroxyethylamino-3-nitrobenzene.

Among the azo direct dyes that may be used according to the invention, mention may be made of the cationic azo dyes described in patent applications WO 95/15144, WO 95/01772, EP 714954, FR 2 822 696, FR 2 825 702, FR 2 825 625, FR 2 822 698, FR 2 822 693, FR 2 822 694, FR 2 829 926, FR 2 807 652, WO 02/078660, WO 02/100834, WO 02/100369 and FR 2 844 269, the content of which forms an integral part of the invention.

Among these compounds, the following dyes may be mentioned most particularly:
1,3-dimethyl-2-[[4-(dimethylamino)phenyl]azo]-1H-imidazolium chloride,
1,3-dimethyl-2-[(4-aminophenyl)azo]-1H-imidazolium chloride,
1-methyl-4-[(methylphenylhydrazono)methyl]pyridinium methyl sulfate.

Among the azo direct dyes that may also be mentioned are the following dyes, described in the Color Index International, 3rd edition:
Acid Yellow 9
Acid Black 1
Basic Red 22
Basic Red 76
Basic Yellow 57
Basic Brown 16
Acid Yellow 36
Acid Orange 7
Acid Red 33
Acid Red 35
Basic Brown 17
Acid Yellow 23
Acid Orange 24.

Mention may also be made of 1-(4'-aminodiphenylazo)-2-methyl-4-bis(β-hydroxyethyl)aminobenzene and 4-hydroxy-3-(2-methoxyphenylazo)-1-naphthalenesulfonic acid.

Among the quinone direct dyes that may be mentioned are the following dyes:
Acid Violet 43
Acid Blue 62
Basic Blue 22
Basic Blue 99
and also the following compounds:
1-N-methylmorpholiniumpropylamino-4-hydroxyanthraquinone
1-aminopropylamino-4-methylaminoanthraquinone
1-aminopropylaminoanthraquinone
5-β-hydroxyethyl-1,4-diaminoanthraquinone
2-aminoethylaminoanthraquinone
1,4-bis(β,γ-dihydroxypropylamino)anthraquinone.

Among the azine dyes that may be mentioned are the following compounds:
Basic Blue 17
Basic Red 2.

Among the triarylmethane dyes that may be used according to the invention, mention may be made of the following compounds:
Basic Green 1
Acid Blue 9
Basic Violet 3
Basic Violet 14
Basic Blue 7
Acid Violet 49
Basic Blue 26
Acid Blue 7.

Among the indoamine dyes that may be used according to the invention, mention may be made of the following compound:
2-β-hydroxyethylamino-5-[bis(β-4'-hydroxyethyl)-amino]anilino-1,4-benzoquinone.

Among the natural direct dyes that may be used according to the invention, mention may be made of carminic acid, kermesic acid, purpurogallin, protocatechaldehyde, isatin, curcumin, spinulosin, apigenidin and orceins. Extracts or decoctions containing these natural dyes, and especially henna-based poultices or extracts, may also be used.

When the composition according to the invention comprises one or more direct dyes, the said composition is then an optionally lightening direct dye composition.

The direct dye(s) preferably represent(s) from 0.001% to 20% by weight approximately, and even more preferentially from 0.005% to 10% by weight approximately relative to the total weight of the dye composition.

When the composition according to the invention does not comprise any dye, but comprises one or more oxidizing agents, the said composition is then a keratin fibre bleaching composition.

For the purposes of the present invention, the term "bleaching" means the total or partial destruction of the natural pigments present in keratin fibres (in particular eumelanins and phaeomelanins).

The composition according to the invention may be in various forms, such as in the form of liquids, creams or gels, or in any other form that is suitable for dyeing or bleaching keratin fibres, and especially human keratin fibres such as the hair.

The present invention also relates to a process for the oxidation dyeing of keratin fibres, and in particular human keratin fibres such as the hair, which consists in applying to the said fibres a dye composition as defined above comprising, as dye(s), one or more oxidation bases, optionally combined with one or more couplers and/or one or more direct dyes, in the presence of one or more oxidizing agents, for a time that is sufficient to develop the desired coloration.

After a leave-on time of from 5 minutes to 1 hour, and preferably from 10 minutes to 1 hour approximately, the keratin fibres are rinsed, washed with shampoo, rinsed again and then dried.

The oxidizing agent may be added to the dye composition just at the time of use, or it may be used starting with an oxidizing composition containing it, which is applied simultaneously with or sequentially to the dye composition.

According to one embodiment, the present invention also relates to a process for the optionally lightening direct dyeing of keratin fibres, and in particular of human keratin fibres such as the hair, which consists in applying to the said fibres a dye composition as defined above comprising, as dye(s), one or more direct dyes optionally in the presence of one or more oxidizing agents, for a time that is sufficient to obtain the desired coloration and optionally the desired lightening.

A subject of the present invention is also a process for bleaching keratin fibres, and in particular human keratin fibres such as the hair, which consists in applying to the said fibres a composition comprising one or more alkanolamines, one or more basic amino acids, one or more additional alkaline agents chosen from aqueous ammonia; ammonium salts of acids whose pKa at 25° C. is greater than 4; alkali metal or alkaline-earth metal hydroxides, carbonates, carbamates and hydrogen carbonates and one or more oxidizing agents; in leaving the composition to act for a leave-on time that is sufficient to obtain the desired bleaching; in removing the composition by rinsing with water, followed by washing with shampoo, and then optionally drying.

The leave-on time ranges between 5 minutes and 1 hour approximately, more preferentially between 10 minutes and 1 hour approximately.

Another subject of the invention is a multi-compartment device for dyeing or bleaching keratin fibres, and in particular human keratin fibres such as the hair. A first compartment contains a composition comprising one or more alkanolamines, one or more basic amino acids, one or more additional alkaline agents chosen from aqueous ammonia; ammonium salts of acids whose pKa at 25° C. is greater than 4; alkali metal or alkaline-earth metal hydroxides, carbonates, carbamates and hydrogen carbonates, and optionally one or more oxidation bases and/or one or more couplers and/or one or more direct dyes, and a second compartment contains an oxidizing composition comprising one or more oxidizing agents.

The examples that follow illustrate the invention without, however, being limiting in nature.

EXAMPLES

In the table below, AM means "active material".

| Composition | Amount (g %) | | | | | | |
|---|---|---|---|---|---|---|---|
| | A | B | C | D | E | F | G |
| Lauric acid | 3 | 3 | 3 | 3 | 3 | 3 | 3 |
| Glycol distearate | 2 | 2 | 2 | 2 | 2 | 2 | 2 |
| Cetylstearyl alcohol (50/50 C16/C18) | 11.5 | 11.5 | 11.5 | 11.5 | 11.5 | 11.5 | 11.5 |
| Oxyethylenated lauryl alcohol (12 EO) | 7 | 7 | 7 | 7 | 7 | 7 | 7 |
| Oxyethylenated oleocetyl alcohol (30 EO) | 4 | 4 | 4 | 4 | 4 | 4 | 4 |
| Oxyethylenated decyl alcohol (3 EO) | 10 | 10 | 10 | 10 | 10 | 10 | 10 |
| Carbomer | 0.4 | 0.4 | 0.4 | 0.4 | 0.4 | 0.4 | 0.4 |
| Silica | 1.2 | 1.2 | 1.2 | 1.2 | 1.2 | 1.2 | 1.2 |
| Propylene glycol | 10 | 10 | 10 | 10 | 10 | 10 | 10 |
| Hexadimethrine chloride as an aqueous 60% solution | 4 (2.4 AM) | 4 (2.4 AM) | 4 (2.4 AM) | 4 (2.4 AM) | 4 (2.4 AM) | 4 (2.4 AM) | 4 (2.4 AM) |
| Dimethyldiallylammonium chloride/acrylic acid copolymer (80/20) as an aqueous 40.5% solution (Polyquaternium-22) | 3 (1.215 AM) | 3 (1.215 AM) | 3 (1.215 AM) | 3 (1.215 AM) | 3 (1.215 AM) | 3 (1.215 AM) | 3 (1.215 AM) |
| DTPA (diethylenetriaminepentaacetic acid, pentasodium salt) as an aqueous 40% solution | 2 (0.8 AM) | 2 (0.8 AM) | 2 (0.8 AM) | 2 (0.8 AM) | 2 (0.8 AM) | 2 (0.8 AM) | 2 (0.8 AM) |
| Sodium metabisulfite | 0.7 | 0.7 | 0.7 | 0.7 | 0.7 | 0.7 | 0.7 |
| Erythorbic acid | 0.3 | 0.3 | 0.3 | 0.3 | 0.3 | 0.3 | 0.3 |

-continued

| Composition | Amount (g %) | | | | | | |
|---|---|---|---|---|---|---|---|
| | A | B | C | D | E | F | G |
| Monoethanolamine | 6.2 | / | 6.2 | 5.4 | 4.5 | 4.2 | 6.2 |
| 2-Amino-2-methyl-1-propanol | / | 1 | / | / | / | / | / |
| Arginine | 5 | 6 | 4 | / | / | / | / |
| Lysine | / | / | / | 5 | 4 | 5 | / |
| Histidine | / | / | / | / | / | / | 4 |
| Aqueous ammonia, as an aqueous solution containing 20% ammonia | 4.5 (0.9 AM) | 5 (1 AM) | / | / | / | / | / |
| Ammonium acetate | / | / | / | / | / | 3 | 4 |
| Ammonium carbonate | / | / | / | 4 | / | / | / |
| Potassium carbonate | / | / | / | / | 2 | / | / |
| Potassium hydroxide | / | / | 1.5 | / | / | / | / |
| para-Phenylenediamine | / | 0.51 | / | 0.3 | 1 | / | 1 |
| 4-Methylaminophenol hemisulfate | / | 0.085 | / | 0.063 | 0.16 | / | 0.16 |
| 1,3-Dihydroxybenzene | / | 0.38 | / | 0.24 | 0.75 | / | 0.75 |
| 1-Hydroxy-3-aminobenzene | / | 0.11 | / | 0.08 | 0.21 | / | 0.21 |
| 1-(β-Hydroxyethyloxy)-2,4-diaminobenzene dihydrochloride | / | 0.025 | / | 0.005 | 0.052 | / | 0.052 |
| 1-Methyl-2-hydroxy-4-(β-hydroxyethylamino)-benzene | / | 0.25 | / | 0.097 | 0.49 | / | 0.49 |
| 1-Hydroxy-4-aminobenzene | 0.545 | 0.23 | 0.545 | 0.17 | 0.44 | 0.545 | 0.44 |
| 1-Methyl-2-hydroxy-4-aminobenzene | 0.615 | 0.05 | 0.615 | 0.057 | 0.1 | 0.615 | 0.1 |
| Fragrance | 0.75 | 0.75 | 0.75 | 0.75 | 0.75 | 0.75 | 0.75 |
| Demineralized water | qs 100 | qs 100 | qs 100 | qs 100 | qs 100 | qs 100 | qs 100 |

The dye compositions A, B, C, D, E, F and G are mixed together at the time of use in a plastic bowl, for 2 minutes, with an aqueous oxidizing composition containing 6% aqueous hydrogen peroxide solution at pH 2.3, at a rate of 1 part by weight of dye composition per 1.5 parts by weight of oxidizing composition.

The mixtures obtained with the dye compositions A, B, C, D and E are applied to locks of natural hair containing 90% white hairs, for 30 minutes at room temperature. The locks are then rinsed with water, washed with a standard shampoo, rinsed again and then dried.

The hair is dyed in more or less strong red-coppery shades for compositions A and C. Furthermore, the hair is not coarse.

The hair is dyed in more or less strong mahogany or red-mahogany shades for compositions B, D and E. Furthermore, the hair is not coarse.

The mixtures obtained with compositions F and G are applied to locks of natural hair containing 90% white hairs, for 10 minutes at room temperature. The locks are then rinsed with water, washed with a standard shampoo, rinsed again and then dried.

The hair is dyed in a strong red-coppery shade for composition F. Furthermore, the hair is not coarse.

The hair is dyed in a strong red-mahogany shade for composition G. Furthermore, the hair is not coarse.

A faint odour of ammonia was also noted for the mixtures obtained from compositions A, B, D, F and G. Compositions C and E have no ammonia odour.

Moreover, a sufficient lightening effect and strong, uniform dyeing are obtained for all the compositions.

The invention claimed is:

1. A cosmetic composition for treating keratin fibers, comprising, in a cosmetically acceptable medium:
   at least one alkanolamine;
   at least one basic amino acid; and
   at least one additional alkaline agents chosen from aqueous ammonia; ammonium salts of acids whose pKa at 25° C. is greater than 4; alkali metal or alkaline-earth metal hydroxides, carbonates, carbamates and hydrogen carbonates;
   wherein the at least one alkanolamine/at least one basic amino acid mole ratio is less than or equal to 10.

2. The composition according to claim 1, in which the at least one alkanolamine is chosen from monoethanolamine, triethanolamine, monoisopropanolamine, diisopropanolamine, N-dimethylaminoethanolamine, 2-amino-2-methyl-1 propanol, triisopropanolamine, 2-amino-2-methyl-1,3-propanediol, 3-amino-1,2-propanediol, 3-dimethylaminol, 2-propanediol and tris(hydroxymethyl)aminomethane.

3. The composition according to claim 2, in which the at least one alkanolamine is monoethanolamine.

4. The composition according to claim 1, in which the at least one basic amino acid is chosen from histidine, lysine, arginine, ornithine and citrulline.

5. The composition according to claim 4, in which the at least one basic amino acid is chosen from histidine, arginine and lysine.

6. The composition according to claim 1, in which the at least one alkanolamine/at least one basic amino acid mole ratio is greater than or equal to 0.1.

7. The composition according to claim 1, in which the at least one ammonium salt is chosen from ammonium salts of a mineral acid or of an organic acid containing from 1 to 7 carbon atoms, having a pKa at 25° C. of greater than 4.

8. The composition according to claim 7, in which the at least one ammonium salt is chosen from ammonium carbonate, ammonium acetate and ammonium hydrogen carbonate.

9. The composition according to claim 1, in which the at least one additional alkaline agent is chosen from aqueous ammonia, ammonium acetate, ammonium carbonate, sodium carbonate, potassium carbonate, sodium hydroxide and potassium hydroxide.

10. The composition according to claim 1, further comprising at least one oxidation base and/or at least one coupler and/or at least one direct dye.

11. The composition according to claim 1, comprising at least one oxidizing agent.

12. A process for dyeing keratin fibers, comprising applying to the fibers a cosmetic composition comprising in a cosmetically acceptable medium:
- at least one alkanolamine;
- at least one basic amino acid; and
- at least one additional alkaline agent chosen from aqueous ammonia; ammonium salts of acids whose pKa at 25° C. is greater than 4; alkali metal or alkaline-earth metal hydroxides, carbonates, carbamates and hydrogen carbonates;

wherein the at least one alkanolamine/at least one basic amino acid mole ratio is less than or equal to 10, wherein the cosmetic composition further comprises at least one oxidation base and/or at least one coupler and/or at least one direct dye, optionally in the presence of at least one oxidizing agent, for a time that is sufficient to develop the coloration and optionally the desired lightening.

13. A process for bleaching keratin fibers, comprising applying to the fibers a cosmetic composition in the presence of at least one oxidizing agent, for a time that is sufficient to obtain the desired bleaching,
wherein the cosmetic composition comprises, in a cosmetically acceptable medium:
- at least one alkanolamine;
- at least one basic amino acid; and
- at least one additional alkaline agent chosen from aqueous ammonia; ammonium salts of acids whose pKa at 25° C. is greater than 4; alkali metal or alkaline-earth metal hydroxides, carbonates, carbamates and hydrogen carbonates;

wherein the at least one alkanolamine/at least one basic amino acid mole ratio is less than or equal to 10.

14. A multi-compartment device for dyeing keratin fibers, comprising
a first compartment containing a composition comprising in a cosmetically acceptable medium:
- at least one alkanolamine;
- at least one basic amino acid; and
- at least one additional alkaline agent chosen from aqueous ammonia; ammonium salts of acids whose pKa at 25° C. is greater than 4; alkali metal or alkaline-earth metal hydroxides, carbonates, carbamates and hydrogen carbonates;

wherein the at least one alkanolamine/at least one basic amino acid mole ratio is less than or equal to 10, wherein the composition further comprises at least one oxidation base and/or at least one coupler and/or at least one direct dye, and
a second compartment containing an oxidizing composition comprising at least one oxidizing agent.

15. A multi-compartment device for bleaching keratin fibers, comprising
a first compartment containing a composition comprising in a cosmetically acceptable medium:
- at least one alkanolamine;
- at least one basic amino acid; and
- at least one additional alkaline agent chosen from aqueous ammonia; ammonium salts of acids whose pKa at 25° C. is greater than 4; alkali metal or alkaline-earth metal hydroxides, carbonates, carbamates and hydrogen carbonates;

wherein the at least one alkanolamine/at least one basic amino acid mole ratio being less than or equal to 10, and
a second compartment containing an oxidizing composition comprising at least one oxidizing agent.

* * * * *